(12) United States Patent
Spencer

(10) Patent No.: US 9,870,761 B2
(45) Date of Patent: Jan. 16, 2018

(54) MUSICAL INSTRUMENT ACTUATORS AND METHODS FOR ACTUATING A MUSICAL INSTRUMENT

(71) Applicant: Robert R. Spencer, Kalispell, MT (US)

(72) Inventor: Robert R. Spencer, Kalispell, MT (US)

( * ) Notice: Subject to any disclaimer, the term of this patent is extended or adjusted under 35 U.S.C. 154(b) by 0 days.

(21) Appl. No.: 15/250,862

(22) Filed: Aug. 29, 2016

(65) Prior Publication Data

US 2017/0061942 A1 Mar. 2, 2017

Related U.S. Application Data

(60) Provisional application No. 62/283,323, filed on Aug. 28, 2015.

(51) Int. Cl.
*G10D 13/02* (2006.01)
*G10D 13/06* (2006.01)

(52) U.S. Cl.
CPC ......... *G10D 13/065* (2013.01); *G10D 13/026* (2013.01)

(58) Field of Classification Search
CPC ............................ G10D 13/026; G10D 13/065
USPC ........................................................ 84/421
See application file for complete search history.

(56) References Cited

U.S. PATENT DOCUMENTS

| | | | | |
|---|---|---|---|---|
| 4,730,532 A * | 3/1988 | Bauerfeind | .......... | G10D 13/065 84/422.1 |
| 5,934,629 A * | 8/1999 | Peritz | ..................... | G10D 13/06 248/121 |
| 6,967,273 B2 * | 11/2005 | Hsieh | ................... | G10D 13/065 84/422.1 |
| 8,153,877 B2 * | 4/2012 | Coady | .................. | G10D 13/065 84/422.1 |
| 8,476,515 B2 * | 7/2013 | Coady | .................. | G10D 13/065 84/422.3 |
| 8,604,325 B2 * | 12/2013 | Sato | ...................... | G10D 13/065 84/422.3 |
| 2006/0060062 A1 * | 3/2006 | Dyk | ...................... | G10D 13/006 84/422.1 |
| 2006/0275631 A1 * | 12/2006 | Rosenberg | ........... | G10D 13/021 429/8 |
| 2011/0107898 A1 * | 5/2011 | Coady | .................. | G10D 13/065 84/422.3 |
| 2011/0265633 A1 * | 11/2011 | Coady | .................. | G10D 13/065 84/422.3 |
| 2012/0118130 A1 * | 5/2012 | Field | ...................... | G10H 3/146 84/730 |
| 2013/0291706 A1 * | 11/2013 | Van Dyk | .............. | G10D 13/006 84/422.3 |
| 2015/0143979 A1 * | 5/2015 | Field | ...................... | G10H 3/146 84/730 |
| 2016/0247492 A1 * | 8/2016 | Field | .................... | G10D 13/024 |
| 2016/0343360 A1 * | 11/2016 | Bailey | .................. | G10D 13/065 |
| 2017/0061942 A1 * | 3/2017 | Spencer | ............... | G10D 13/065 |

* cited by examiner

*Primary Examiner* — David Warren
*Assistant Examiner* — Christina Schreiber
(74) *Attorney, Agent, or Firm* — Wells St. John P.S.

(57) ABSTRACT

This disclosure includes a first magnet and a second magnet spaced from the first magnet in a repulsive relationship. A rod is configured to be secured to a musical instrument and is in a corresponding relationship with the first and second magnets. The corresponding relationship is defined as the movement of the rod corresponds to movement between the first and second magnets.

20 Claims, 7 Drawing Sheets

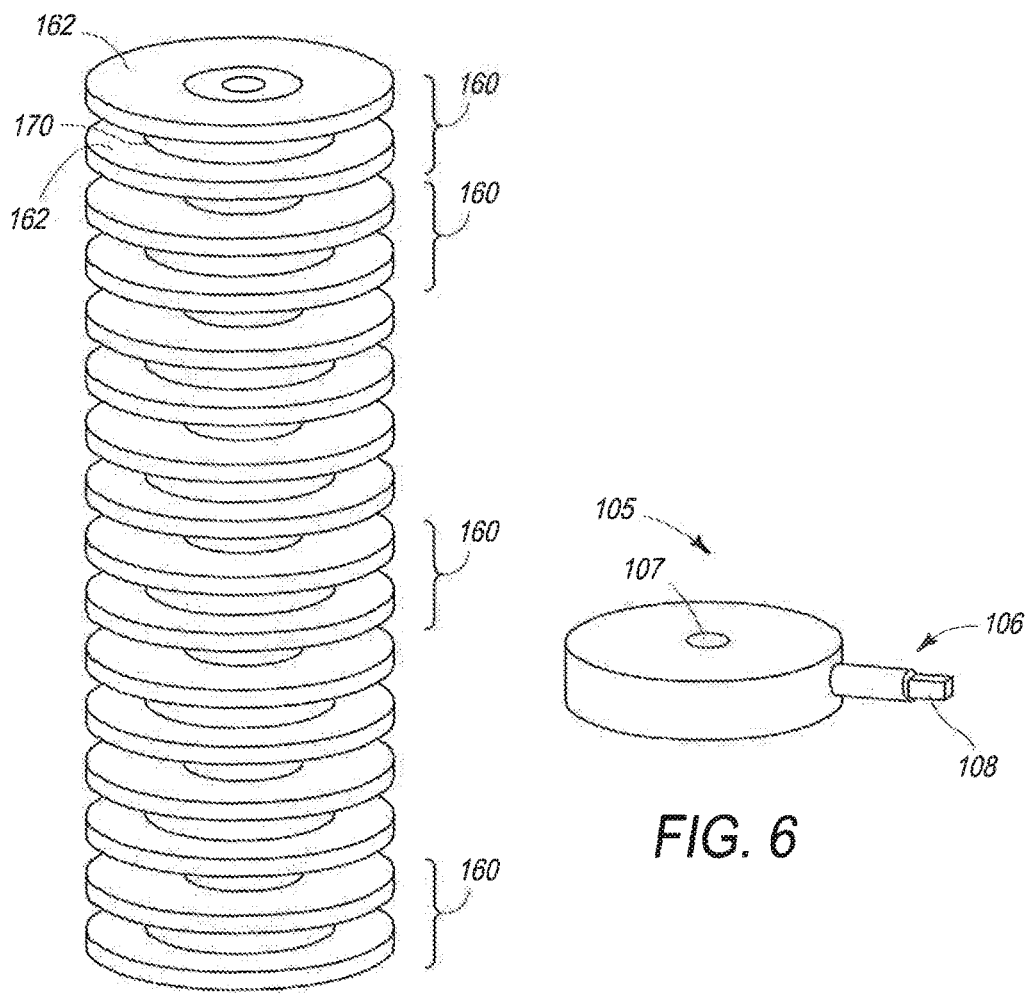
FIG. 4
FIG. 6
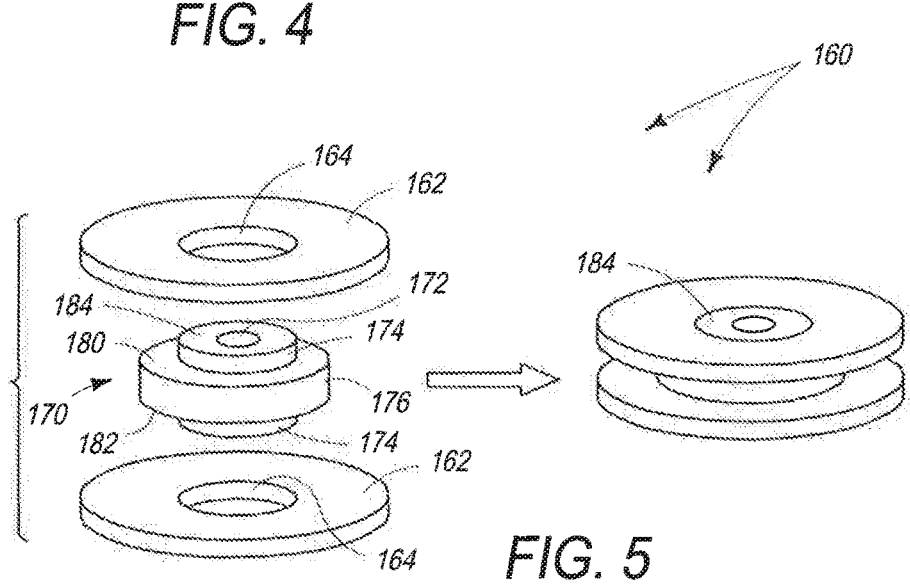
FIG. 5

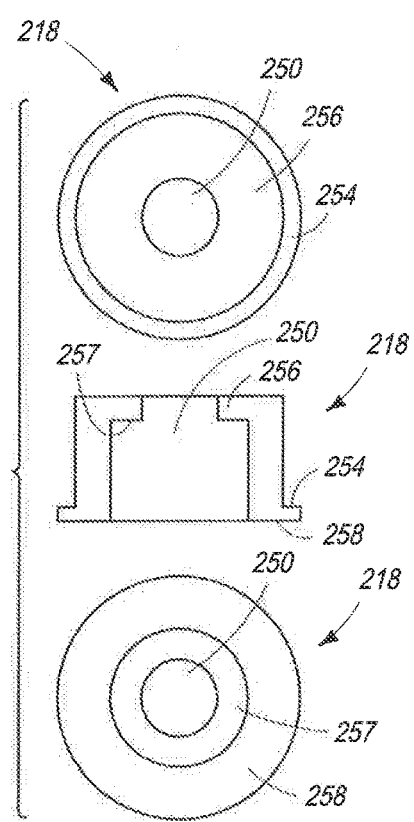
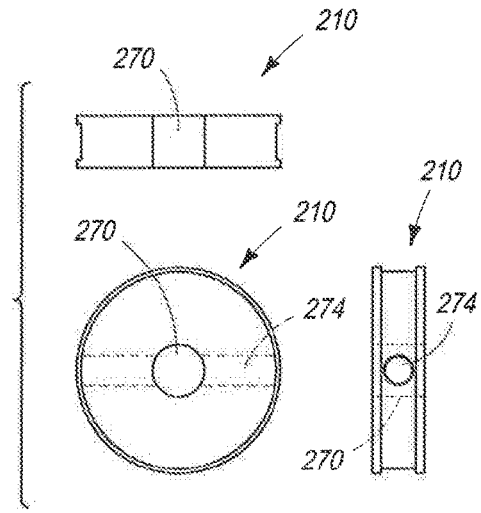
FIG. 8A
FIG. 8B
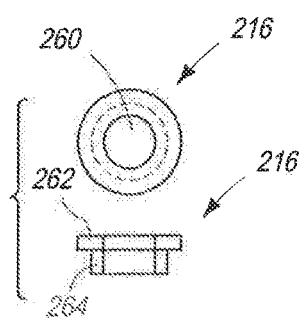
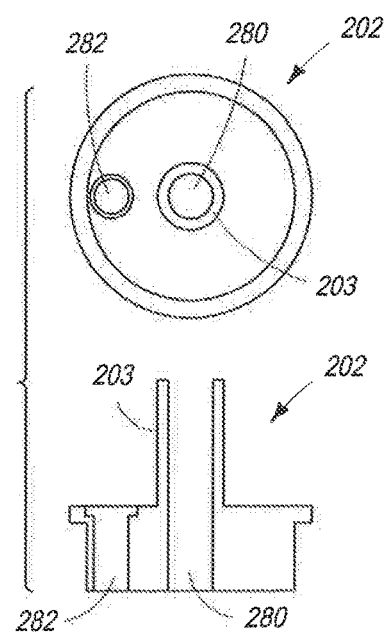
FIG. 8C
FIG. 8D

MUSICAL INSTRUMENT ACTUATORS AND METHODS FOR ACTUATING A MUSICAL INSTRUMENT

CROSS REFERENCE TO RELATED APPLICATION

This application claims priority from U.S. Provisional Patent Application 62/283,323 filed Aug. 28, 2015, the disclosure of which is incorporated herein by reference.

TECHNICAL FIELD

The subject matter of this application relates to musical instrument actuators and methods for actuating a musical instrument.

BACKGROUND OF THE DISCLOSURE

While the subject matter of this application was motivated in addressing musical instrument actuators and methods, it is in no way so limited. The disclosure is only limited by the accompanying claims as literally worded, without interpretative or other limiting reference to the specification, and in accordance with the doctrine of equivalents.

Other aspects and implementations are contemplated.

Improvements to musical instruments are always needed to consistently produce the desired characteristic quality of a musical sound.

BRIEF DESCRIPTION OF THE DRAWINGS

Exemplary embodiments of the various disclosures are described below with reference to the following accompanying drawings. The drawings may be considered to represent scale.

FIG. 4 is a perspective view of a collection of the magnetic assemblies of the actuator of FIGS. 2A and 2B;

FIG. 5 is a perspective view of a magnetic assembly of the actuator of FIGS. 2A and 2B;

FIG. 6 is a perspective view of a locking collar of the actuator of FIGS. 2A and 2B;

FIGS. 8A to 8F are various views of the components and structures for the actuator of FIG. 7.

DETAILED DESCRIPTION OF THE EMBODIMENTS

This disclosure is submitted in furtherance of the constitutional purposes of the U.S. Patent Laws "to promote the progress of science and useful arts" (Article 1, Section 8).

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

A common musical instrument used in many ensembles is a cymbal. A cymbal is a percussion instrument and routinely used in pairs. The construction of a cymbal includes a thin, normally round plate of various metals or alloys. The majority of cymbals are of indefinite pitch but a smaller diameter cymbal can have a more definite pitch. Various ensembles using cymbals include orchestras, percussion ensembles, jazz bands, heavy metal bands, and marching groups.

An integral part of a drummer's kit is at least one or more of various configurations or combinations of cymbals which can include a crash cymbal, a ride cymbal or crash/ride cymbal, and/or a hi-hat which is a stand or system of a pair of cymbals.

Figure 1:
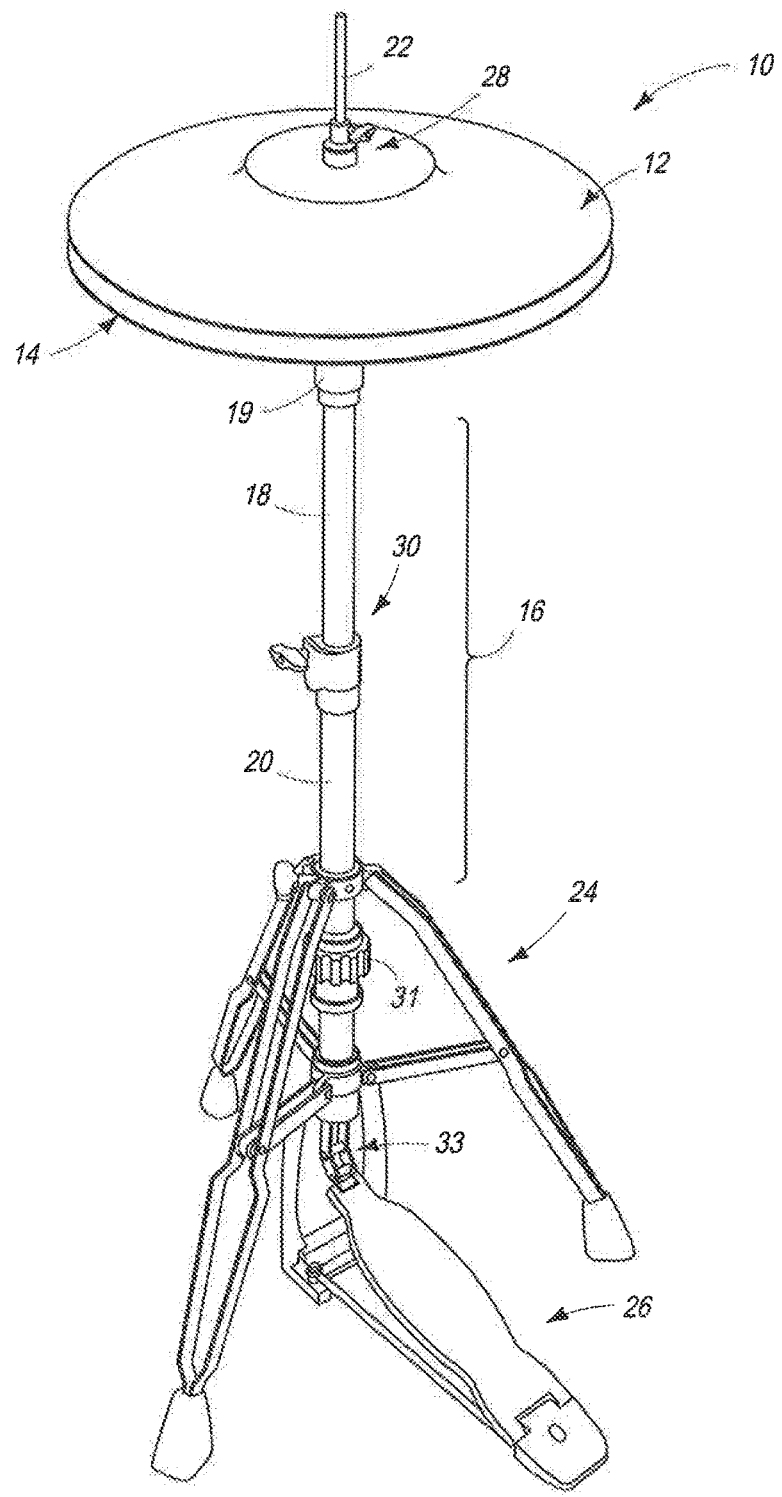
FIG. 1 is perspective view of an embodiment of a cymbal system.

FIG. 1 illustrates an embodiment of an exemplary cymbal system 10 having a pair of cymbals. The cymbal system 10 features two cymbals, an upper (top or first) cymbal 12 positioned over, and spaced from, a lower (bottom or second) cymbal 14. Typically, the two cymbals are fourteen inches (14") in diameter. The lower cymbal 14 is cupped upward while the upper cymbal 12 is cupped downward. Both cymbals 12, 14 are mounted on a stand that includes several components. One exemplary stand includes a tube assembly or tube structure 16 and a pull rod 22 coaxially extending through at least a portion of the tube structure 16. An uppermost portion of the pull rod 22 is exposed from the tube structure 16 and extends through the center of the cymbals 12, 14 to terminate elevationally above the cymbals 12 and 14. The lower cymbal 14 is stationary and supported upon the tube structure 16 while the upper cymbal 12 is secured to (or connected or linked to) the pull rod 22 via a clutch assembly 28. The tube structure 16 is supported upon a tripod 24.

In one exemplary embodiment, the tube structure 16 comprises an upper tube (upper column) 18 slidingly engaging (coaxially engaging) a lower tube (lower column) 20 which has a larger diameter to receive the upper tube 18. This sliding engagement allows for the height of the cymbals 12, 14 to be adjusted 30 relative to a support surface such as a floor.

Still referring to FIG. 1, a foot pedal (or pedal board) 26 has a first end supported upon the floor and an opposite second end (front end) elevationally spaced above the floor. Linkage 33 pivotally secures (connects or hinges) the second end of the foot petal 26 ultimately to the pull rod 22. In the rest position, the foot pedal 26 is angled relative to the floor having the second end elevationally above the floor. Reciprocal movement of the second end of the foot pedal upward and downward relative to the floor provides corresponding reciprocal movement upward and downward of the pull rod 22 through the tube structure 16. The reciprocal movement of the pull rod 22 upward and downward correspondingly moves the upper cymbal 12 vertically upward away from the lower cymbal 14 and vertically downward to contact the lower cymbal 14. It should be understood that in the rest position for cymbal system 10, the upper cymbal 12 is in the upward-most position spaced from the lower cymbal 14.

Still referring to FIG. 1, a spring unit (or spring assembly) is inside the tube assembly 16, and therefore, not shown. An exemplary spring device in the spring unit is a coil spring (or helical spring) and is provided in a relationship to constantly apply an upward force to the pull rod 22. This constant force by the spring unit maintains the cymbal system 10 in the rest position with the upper cymbal 12 in the spaced relation to the lower cymbal 14. In one embodiment, the cymbal system 10 includes a tension control mechanism 31 which in this embodiment is located in the lower tube 20. The tension control mechanism 31 cooperates with the spring unit to provide the capability of selectively increasing and decreasing the tension in the spring device of the spring unit.

Adjusting the tension control mechanism 31 to increase the tension in the spring device increases the pressure needed to be applied to the foot pedal 26 to move the upper cymbal 12. Alternatively, adjusting the tension control mechanism 31 to decrease the tension in the spring device decreases the pressure needed to be applied to the foot pedal 26 to move the upper cymbal 12.

As stated previously for the rest position of the cymbal system 10, the foot pedal 26 is angled relative to the floor with the front end (second end) of the foot pedal 26 elevationally spaced above the floor. Additionally in this rest position, the upper cymbal 12 is spaced from the lower cymbal 14. In operation of the cymbal system 10, pressure is applied to the foot pedal 26 from the rest position directing the front end of the foot pedal downward toward the floor. This action on the foot pedal 26 compresses the spring device in the spring unit and drives the pull rod 22 downward and drives the upper cymbal 12 downward toward the lower cymbal 14 to ultimately contact the lower cymbal 14. Releasing or diminishing the pressure on the foot pedal 26 (or raising the foot way from the foot pedal) allows the spring device to move or force all the previously described structure in motion to move in the opposite direction towards the original resting position. That is, the front end of the foot pedal 26, the pull rod 22 and the upper cymbal 12 reverse direction to move upward away from the floor, and ultimately, to move the upper cymbal 12 away from the lower cymbal 14.

However, using a coil spring as the spring device for the cymbal system 10 has all the problems associated with a coil spring. That is, under repetitive use and strain (load), creep and fatigue can develop in the spring device. Creep is the permanent deformation over time and fatigue is crack propagation over time. Both occur due to applied loads to the spring device continually compressing and elongating the spring device which leads to failure or at least diminishes the functionality of the spring device. Diminished functionality means consistent music quality or characteristic (tone) of the cymbal system 10 is diminished and/or ultimately lost.

Referring to FIGS. 2-6, an inventive embodiment of a cymbal system is illustrated that includes an actuator unit (drive unit, return unit, return actuator, magnetic drive unit or actuator) 100 to replace the coil spring as the spring device for the spring unit. Accordingly, actuator unit 100 resolves the above-noted problems with the cymbal system 10 having a coil spring.

It should be understood that the same components and structures described for cymbal system 10 used in the figures for this embodiment of cymbal system with actuator 100 will have the same reference numbers as presented in FIG. 1 and will not be described again. Moreover, it should be understood that while many of the same components and structures described for cymbal system 10 are not shown in the figures for this embodiment of cymbal system with actuator 100, it is understood that the "not shown" components and structures may exist for the cymbal system with actuator 100.

Figure 2A:
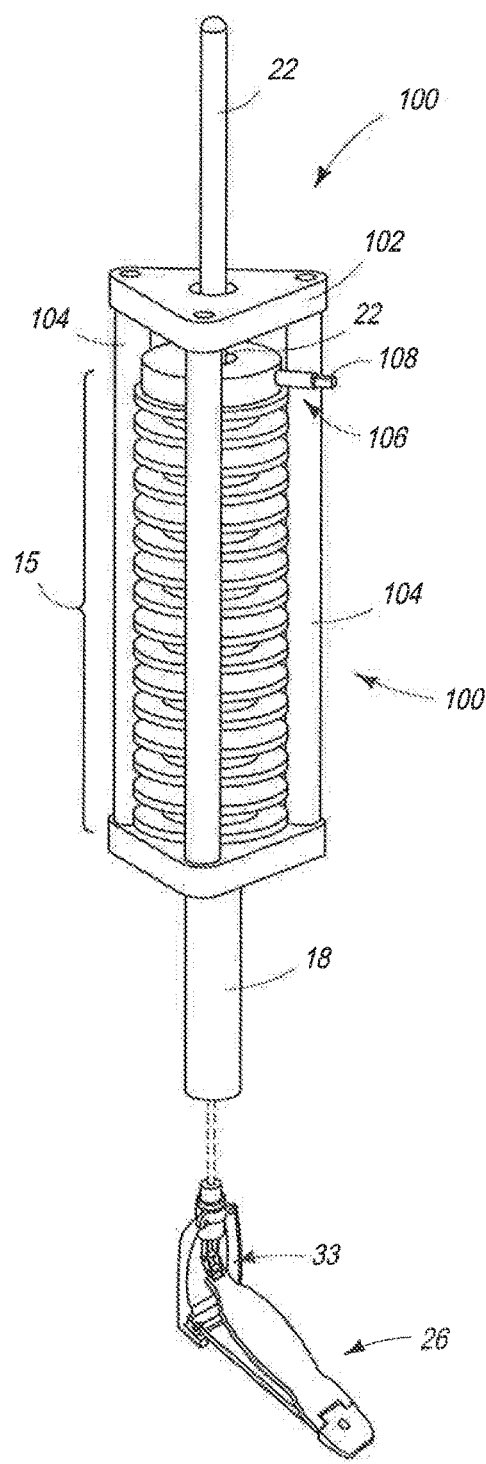
FIGS. 2A and 2B are perspective views of an embodiment of an actuator for a cymbal system.
Figure 2B:
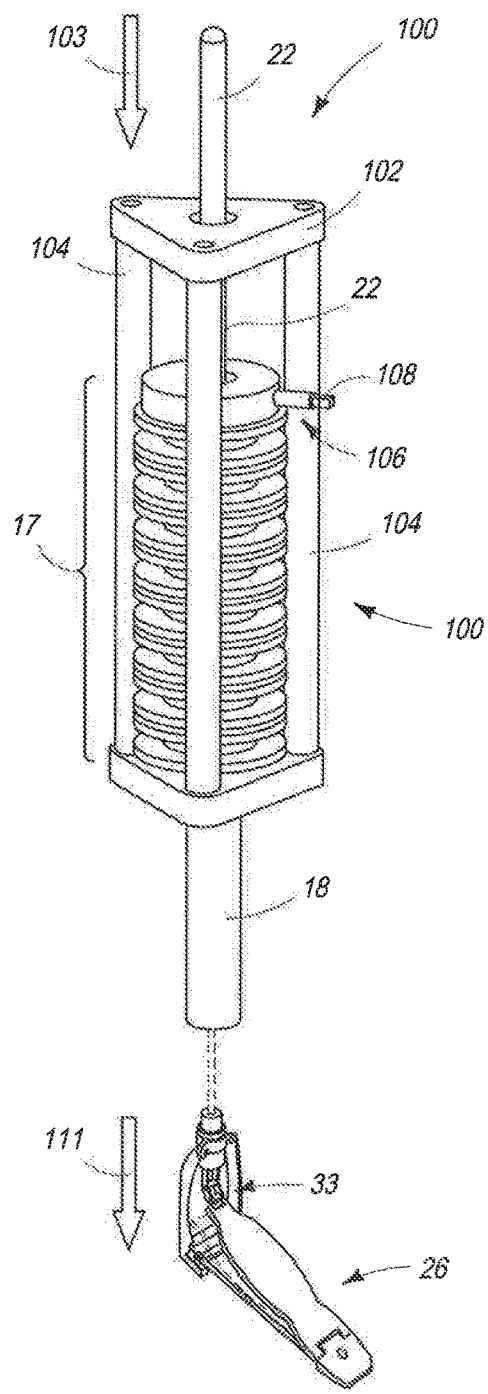

Referring to FIG. 2A, the exemplary actuator 100 is shown to be coaxially aligned with the pull rod 22 and the upper tube 18 of a tube structure. It is to be understood that the pull rod 22 is ultimately secured to, without specifically showing the structure already presented in FIG. 1, the linkage 33 and front end of foot pedal 26. FIG. 2A illustrates this embodiment of the cymbal system with actuator 100 in the rest position wherein a collection of magnetic assemblies (referenced as 160 in other figures) occupies a length dimension 15 in the actuator 100. FIG. 2B illustrates the action of the cymbal system and actuator 100 in use wherein a force is applied to the foot pedal 26 in the downward direction 111 toward the support surface (floor). This action moves the pull rod 22 in the downward direction 103 diminishing the length dimension of the collection of the magnetic assemblies (referenced as 160 in other figures) to occupy a smaller length dimension 17 in the actuator 100.

It should be understood that once the foot pedal 26 is released or the force to the foot pedal diminished enough to allow the foot petal 26 to move in an opposite direction (an upward direction) to direction 111, then the pull rod 22 will move in an opposite direction (an upward direction) to direction 103. Ultimately, the cymbal system with actuator 100 can move back to the rest position shown in FIG. 2A. The function and action of the cymbal system with actuator 100 is described more thoroughly subsequently.

Figure 3:
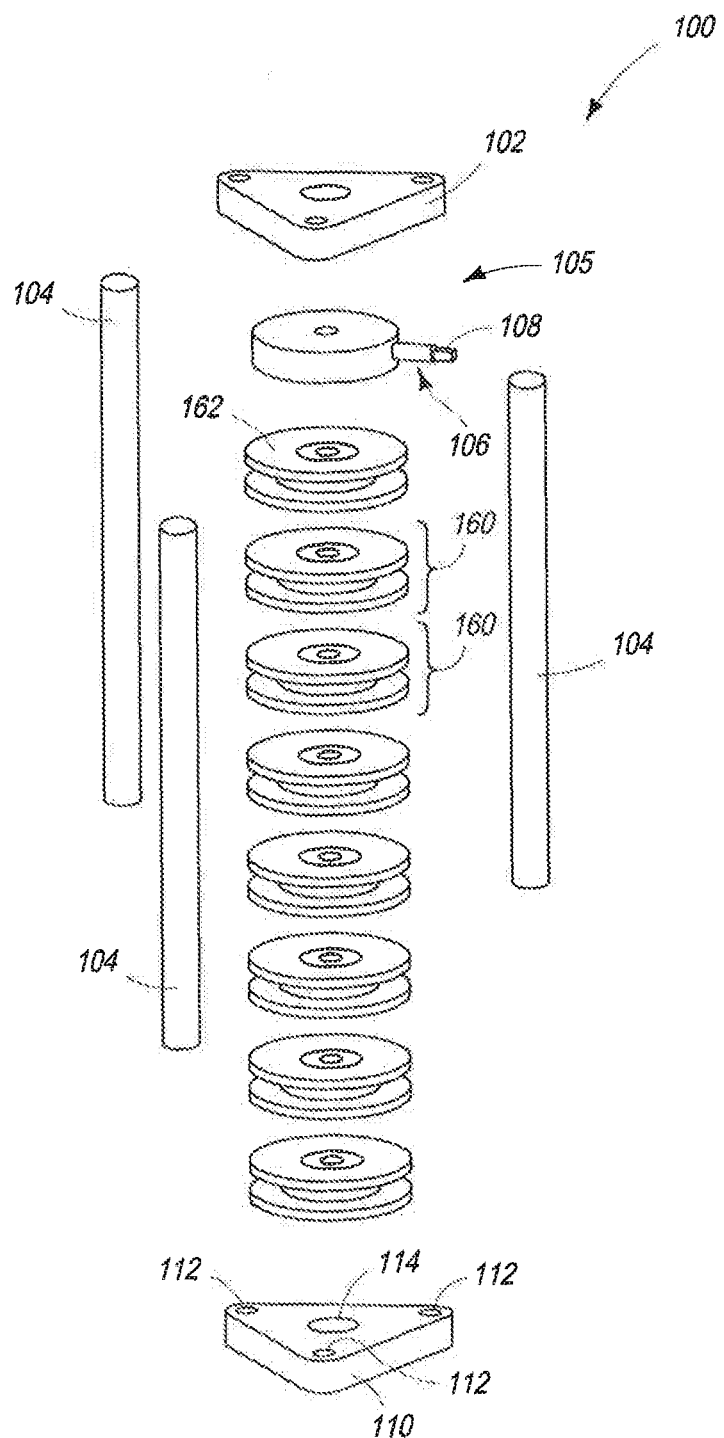
FIG. 3 is an exploded view of the actuator of FIGS. 2A and 2B.

Referring to FIG. 3, actuator 100 includes two or more magnetic assemblies (or magnet units, magnetic units, magnet assemblies) 160. Each exemplary magnetic assembly 160 includes a bushing (or spacer) 170 between a pair of magnets 162. The magnetic assemblies 160 are aligned vertically and coaxially with the pull rod 22 and the upper tube 18. The magnetic assemblies 160 are oriented so each magnet 162 is oriented in a repulsive state or relationship (or repelling state or relationship) relative to the magnets 162 of an adjacent magnetic assembly 160. That is, the north pole of each magnet 162 in a magnetic assembly 160 faces the north pole of an adjacent magnet 162 in an adjacent magnetic assembly 160. Alternatively, the south pole of each magnet 162 in a magnetic assembly 160 faces the south pole of an adjacent magnet 162 in an adjacent magnetic assembly 160. Accordingly, in this repulsive state, a space between each magnetic assembly 160 is naturally maintained by the magnetic power of each magnet 162 assuming no additional force is acting upon the magnetic assemblies 160 other than gravity. Correspondingly, the spacing distance between each magnetic assembly 160 depends on the magnetic power, repulsive or attractive, of the magnets 162 in the magnetic assembly 160.

It should be understood throughout this document that for a pair of magnets in a repulsive state or relationship, the repulsive force on the pair of magnets will result in the pair attempting to maintain a spacing or distance between the magnets. As the distance or spacing between the pair of magnets is shortened or diminished, the repulsive force is increased.

Referring to FIGS. 4-5, as stated previously, each exemplary magnetic assembly 160 includes a bushing 170 between a pair magnets 162. Each magnet 162 is circular with a central opening 164. Each bushing 170 has a central portion 176 and end portions 174 extending outwardly from opposite sides of the central portion 176. The two end portions 174 have the same diameters and are centrally located on central portion 176. The two end portions 174 have smaller diameters than the central portion 176. Referring to FIG. 4, if each magnetic assembly 160 has the same magnets 162, or magnets with the same magnetic power, then the spacing between each magnet assembly 160 will be the same distance when vertically aligned under the force of gravity. In other embodiments of the cymbal system, one or more magnets will be a different type or composition having a different magnetic power relative to at least one other of the magnets in the cymbal system meaning all the distances between the magnetic assemblies will not be the same.

Still referring to FIGS. 4-5, each magnet 162 of a pair has the centrally located opening 164 received over the end portions 174 of each bushing 170. The central portion 176 has a pair of opposite circular ridges (or support surfaces) 180, 182 extending from respective end portions 174 to receive or support respective magnets 162. Each bushing 170 has a centrally-located opening 172 configured to receive pull rod 22. Each end portion 174 of bushings 170 will have a surface 184 that is exposed through openings 164 of respective magnets 162 when the components of the magnet assemblies 160 are fitted together. Material for bushings 170 can be metallic (magnetic or nonmagnetic), plastic, polymers, fiberglass, wood, cloth, rubber, felt, ceramic, stainless steel and polyethylene.

It should be understood that since the magnetic assemblies 160 are oriented in a repulsive state relative to each other, each pair of magnets 162 for each one magnetic assembly 160 are in an attractive relationship or state. Accordingly, the pair of magnets 162 for one magnetic assembly 160 are held onto the bushing 170 by the attractive power of the respective magnets 162.

Referring to FIG. 3, an exploded view of the actuator 100 shows various exemplary components or structures. To house the magnet assemblies 160, actuator 100 includes two or more support columns 104 and top (upper) and bottom (lower or base) flanges 102, 110. Each support column 104 has a circular cross section and has a threaded opening (not shown) in each end. In this exemplary embodiment of the actuator 100, three support columns 104 are provided with other possible numbers of support columns 104 contemplated including only two support columns and four or more support columns 104. The respective flanges 102, 110 are configured as triangles having corner openings 112 at each of the three corners of the flanges 102, 110. Each flange 102, 110 also has a central opening 114 to receive pull rod 22 or an extension of pull rod 22. The top flange 102 is aligned vertically over, and spaced from, the bottom flange 110 with the respective corner openings 112 being aligned. Each support column 104 is positioned between respective flanges 102, 110 with each end of each one support column 104 being provided over aligned corner openings 112. Bolts (not shown) are provided through each corner opening 112 of the flanges 102, 110 and threaded into the threaded opening in the end of the support column 104 aligned over the aligned corner openings 112. A lowermost magnet assembly 160 is supported by the bottom flange 110 and may, or may not, be positioned against, or in contact with, the bottom flange 110.

A washer or spacer (not shown) can be provided between the lowermost magnet assembly 160 and the bottom flange 110. An exemplary material for the washer or spacer can be plastic, polymers, fiberglass, wood, cloth, rubber, polyethylene, and/or felt. An exemplary material for support column 104 can be metallic (magnetic or nonmagnetic), plastic, polymers, fiberglass, wood, ceramic, stainless steel and polyethylene. An exemplary material for flanges 102, 110 can be metallic (magnetic or nonmagnetic), plastic, polymers, fiberglass, wood, ceramic, stainless steel and polyethylene.

Still referring to FIG. 6, an exemplary locking collar (or clamp, locking clamp) 105 is illustrated. The locking collar 105 is positioned between the uppermost magnetic assembly 160 and the top flange 102 and may, or may not, be positioned against, or in contact with, the top flange 102. The locking collar 105 includes a locking screw 106 having a square head 108. The locking collar 105 includes a central opening 107 configured to receive the pull rod 22. The square head 108 is configured to be rotated to move the locking screw 106 linearly. As an example, clockwise rotation of the square head 108 (that is, tightening the locking collar 105) moves the locking screw 106 linearly toward, and into, the opening 107 of locking collar 105 to ultimately contact the pull rod 22 thereby tightening the locking collar 105 in place to the pull rod 22. Alternatively, counterclockwise rotation of the square head 108 (that is, loosening the locking collar 105) moves the locking screw 106 linearly away from, and out of, the opening 107 of locking collar 105 to ultimately release contact of the pull rod 22 thereby loosening the locking collar 105 from being locked in place to the pull rod 22.

Referring to FIG. 2A, the pull rod 22 is shown provided through the center of the magnetic assemblies 160 and the locking collar 105. The function of the locking collar 105 of actuator 100 is to set, and provide the capability to selectively adjusting, the spacing between each magnetic assembly 160. Selecting the position of the locking collar 105 along the length of the pull rod 22 selects the location of the topmost magnetic assembly 160 along the length of the pull rod 22, and thereby, selects the spacing between each magnetic assembly 160. Without the locking collar 105, the magnetic assemblies 160 can move freely along the length of the pull rod 22. Moreover, wherein the locking screw 106 is not locked or tightened onto the pull rod 22, the locking collar 105 also moves freely along the length of the pull rod 22. That is, in operation, as the locking screw 106 is rotated clockwise (tightening), an end of the locking screw 106 is moved toward the pull rod 22 until contact is made with the pull rod 22. Continued clockwise rotation of the locking screw 106 increases the pressure of the locking screw 106 onto the pull rod 22 until the locking collar 105 is locked at a desired location along the length of the pull rod 22. That is, the locking collar 105 is no longer free to move along the length of the pull rod 22.

Accordingly, the locking collar 105 can be forced onto the topmost magnetic assembly 160 and forced downward to compress or shorten (diminish) the respective distances (spacing) between the respective magnetic assemblies 160. That is, once a desired location of the locking collar 105 along the length of the pull rod 22 is selected, which corresponds to a selected spacing desired between the respective magnetic assemblies 160, the locking screw 106 is tightened (rotated clockwise) onto the pull rod 22 to maintain the selected position of the locking collar 105 along the length of the pull rod 22. In this state, the magnetic assemblies 160 will be in a compressed state relative to a natural spacing state meaning that the repulsive force has increased between respective magnetic assemblies 160.

It should be understood that in this compressed state, the actuator 100 is functioning the same as the tension control mechanism 31 described previously for the cymbal system 10 of FIG. 1. Accordingly, actuator 100 provides the capability of selectively increasing and decreasing the pressure needed to be applied to the foot pedal 26 to move the upper cymbal 12. Alternatively, moving the locking collar 105 along the length of the pull rod 22 toward the top flange 102 decreases the pressure needed to be applied to the foot pedal 26 to move the upper cymbal 12. Consequently, the tension control mechanism 31 described previously for the cymbal system 10 is not needed for this embodiment of the cymbal system with the actuator 100.

It should be understood that the locking collar 105 can be provided between the lowermost magnetic assembly 160 and the bottom flange 110 and may, or may not, be positioned against, or in contact with, the bottom flange 110. The purpose and function of the locking collar 105 is the same in either position. It should be further understood that an exemplary washer or spacer (not shown) explained previously as possibly being between the lowermost magnetic assembly 160 and the bottom flange 110 can also be between the uppermost magnetic assembly 160 and the locking collar 105, and/or between the locking collar 105 and the top flange 102.

Figure 7:
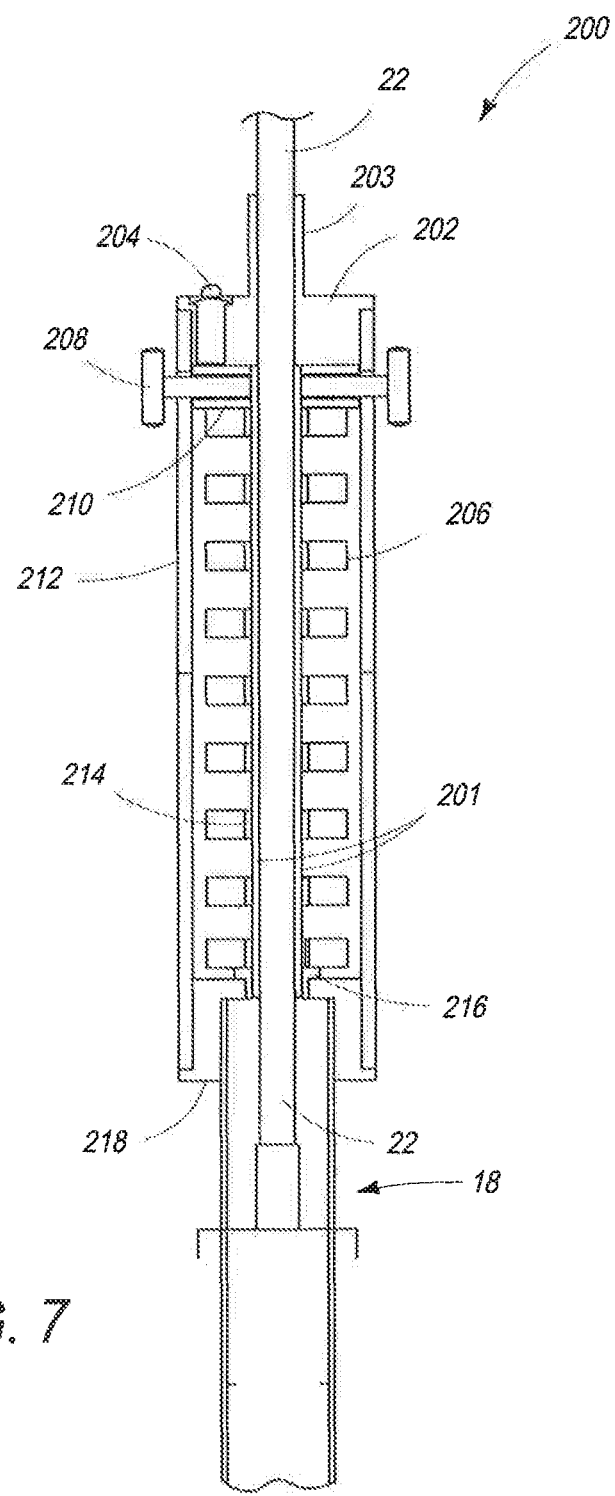
FIG. 7 is a sectional view of an embodiment of an actuator for a cymbal system.

Referring to FIGS. 7-9, another inventive embodiment of a cymbal system is illustrated that includes an actuator unit (drive unit, return unit, return actuator, magnetic drive unit or actuator) 200 to replace the coil spring as the spring device for the spring unit described with respect to cymbal system 10 of FIG. 1. Accordingly, actuator unit 200 resolves the above-noted problems with the cymbal system 10 having a coil spring.

It should be understood that the same components and structures described for cymbal system 10 used in the figures for this embodiment of cymbal system with actuator 200 will have the same reference numbers as presented in FIG. 1 and will not be described again. Moreover, it should be understood that while many of the same components and structures described for cymbal system 10 are not shown in the figures for this embodiment of cymbal system with actuator 200, it is understood that the "not shown" components and structures may exist in the cymbal system with actuator 200.

Referring to FIG. 7, the exemplary actuator 200 has a collection of magnets 206 but no magnetic assemblies 160 that exist in actuator 100. Accordingly, actuator 200 does not have the bushing 170 of actuator 100 nor the pair of magnets 162 associated with each bushing 170. That is, actuator 200 only has spaced magnets 206. Magnets are coaxially aligned with the pull rod 22, upper tube 18, and an inner tube 201 (which is provided over pull rod 22). It is to be understood that the pull rod 22 is ultimately secured to the linkage 33 secured to the front end of foot pedal 26 as described in FIG. 1 with cymbal system 10. Magnets 206 are ring shaped and have central openings 214 that are received over the inner tube 201 and the inner tube 201 is received over, as stated previously, the pull rod 22.

Still referring to FIG. 7, magnets 206 are capable of moving freely along the length of the inner tube 201 and along the length of the pull rod 22. Each magnet 206 is oriented in a repulsive (repelling) relationship relative to each other adjacent magnet 206. That is, for one magnet, if the top surface of the one magnet is its north pole and the opposite bottom side is its south pole, then the top surface of the one magnet faces the north pole of an adjacent magnet and the bottom surface of the one magnet faces the south pole of an adjacent magnet. Accordingly, a natural spacing between respective magnets 206 exists along the length of the inner tube 201.

It should be understood that actuator 200 of FIG. 7 is illustrated in the rest position. Alternatively, when the cymbal system with actuator 200 is in use wherein a force is applied to the foot pedal 26 in a downward direction, the pull rod 22 is pulled in the downward direction. As the pull rod 22 is pulled downward, the collection of magnets 206 move collectively in the downward direction with the spacing (distance) between each magnet 206 diminishing. Consequently, the repulsive force between respective magnets 206 is increased and is directed upward in the opposite direction to the downward motion of the pull rod 22. It should be understood that once the foot pedal 26 is released or the force to the foot pedal diminished enough to allow the foot petal 26 to move in an upward direction, the actuator 200 will ultimately return to the rest position under the power of the repulsive force of the magnets 206.

Figures 8E, 8F:
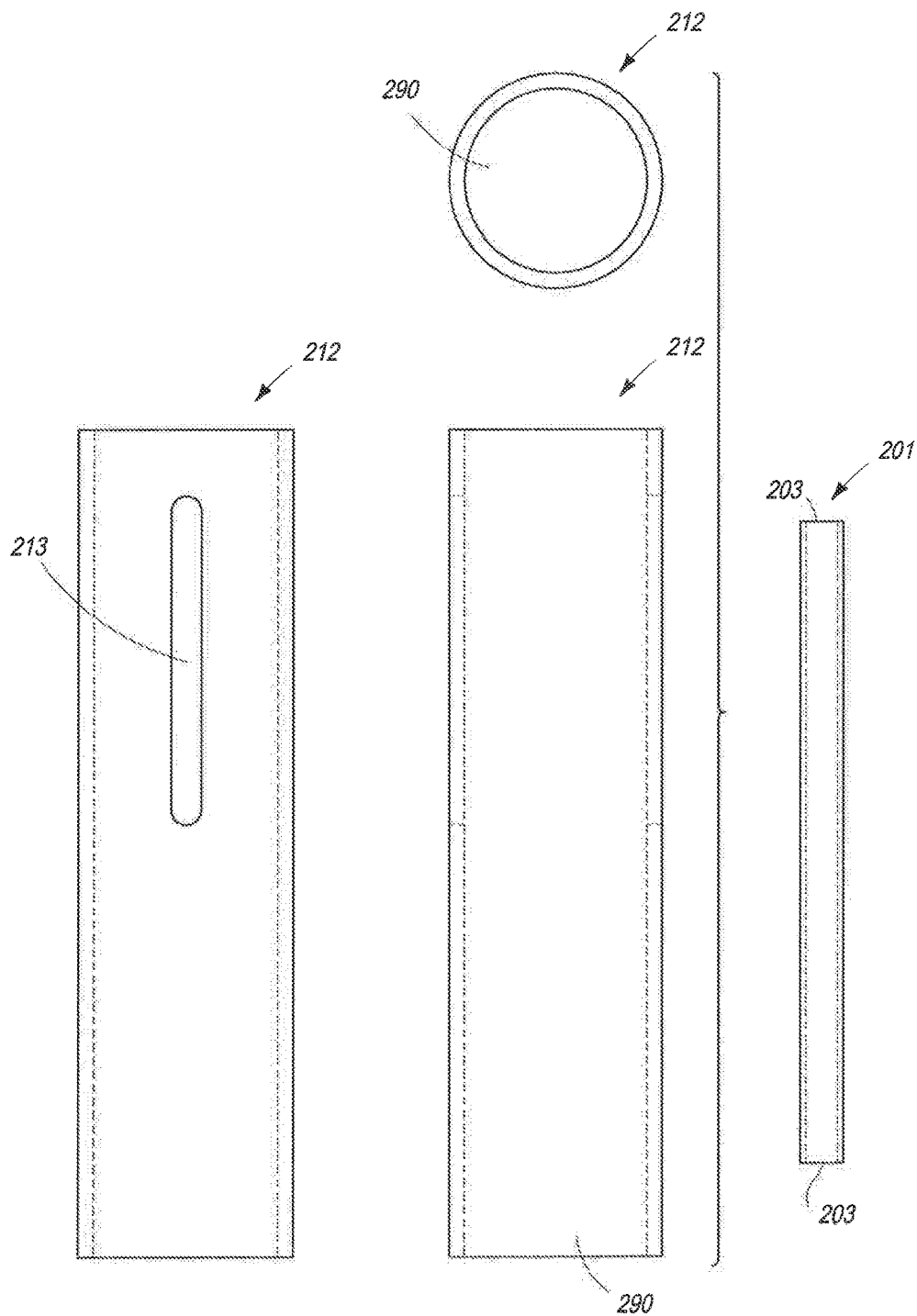

Inner tube 201 is singularly shown in FIG. 8F and has an interior 203 to receive pull rod 22.

Referring to FIG. 7, magnets 206, inner tube 201 and a portion of pull rod 22 are housed in an outer tube 212 singularly shown in FIG. 8E. Magnets 206, inner tube 201 and the portion of pull rod 22 are received in the interior 290 of outer tube 212. A slot 213 extends longitudinally and entirely through the wall structure of the outer tube 212 (that is, from the exterior to the interior 290). Directly across from slot 213 is a second slot with the same configuration and dimensions.

Referring to FIG. 7, a seat unit 202 is secured in the open top end of the outer tube 212 with pull rod 22 configured to slide through the seat unit 202. Seat unit 202 is singularly shown in FIG. 8D. Seat unit 202 has a chimney or stack portion 203 extending from a base. An opening 280 extends through stack portion 203 and base. Opening 280 receives pull rod 22. Base of seat unit 202 also has another opening 282 to receive tilt mechanism 204. Seat unit 202 will support cymbal 12, or both cymbal 12 and cymbal 14. Tilt mechanism 204 is used to selectively tilt cymbal 12, or both cymbal 12 and cymbal 14.

Referring to FIG. 7, a locking disk 210 is positioned below seat unit 202 and above the topmost magnet 206. Locking disk 210 is secured to the uppermost portion of the inner tube 201. Locking disk 210 is configured to slide freely through the inner diameter (interior 290) of outer tube 212. A pair of locking screws 208 extends from opposite sides of locking disk 210 and each is capable of contacting pull rod 22. Locking disk 210 is singularly shown in FIG. 8B (without locking screws 208). A central opening 270 in locking disk 210 receives pull rod 22. A pair of openings 274 extend through opposite sides of the locking disk 210 perpendicularly to the central openings 270. Openings 274 receive the locking screws 208.

It should be understood that the locking disk 210 with locking screws 208 of actuator 200 functions in the same manner, and has the same purpose, as the locking collar 105 with locking screw 106 of actuator 100. Accordingly, that detailed description of the function and purpose is not provided here. The locking screws 208 extend through the slots 213 of the outer tube 212 and are rotated to selectively tighten and loosen the locking disk 210 at the selective position in the outer tube 212 and relative to pull rod 22. As the pull rod 22 is driven up and down, the locking screws 208 move up and down through the slots 213. That is, the locking screws 208 are available from the outside of the outer tube 212 for the purpose of adjusting both the tension in the foot pedal 26 and positioning of the locking disk 210 along the length of the pull rod 22.

It should be further understood that the locking disk 210 of the actuator 200 functions in the same manner as the tension control mechanism 31 described previously for the cymbal system 10 of FIG. 1. As stated previously, the actuator 200 provides the capability of selectively increasing and decreasing the pressure needed to be applied to the foot pedal 26 to move the upper cymbal 12. Consequently, the tension control mechanism 31 described previously for the cymbal system 10 is not needed for this embodiment of the cymbal system with the actuator 200.

Referring to FIG. 7, a stop bushing 216 impedes further movement of a lowermost magnet 206 through outer tube 212. Stop bushing 216 is singularly shown in FIG. 8C. Stop bushing 216 has an upper portion 262, a lower portion 264, and a central opening 260 to receive pull rod 22.

Referring to FIG. 7, a closure bushing 218 is provided in the bottom opening of outer tube 212 and is singularly shown in FIG. 8A. Closure bushing 218 has an interior 250. A first end of the closure bushing 218 has an opening to receive the lower portion 264 of the stop bushing 216. A second end 258 of the closure bushing 218, opposite the first end, receives the top portion of the upper tube 18 and secures that top portion of the upper tube 18 in the bottom portion of the outer tube 212. A terminal end of upper tube 18 abuts against an interior surface 257 of closure bushing 218. The upper portion 262 of the stop bushing 216 rests upon an exterior upper surface 256 of closure bushing 218 between the lowermost magnet 206 and closure bushing 218. An exterior surface of a ridge 254 of closure bushing 218 rests against a bottom end of outer tube 212.

As stated previously, a coil spring is used in cymbal system 10 to return the system to the rest state with the top cymbal spaced above the bottom cymbal. As further stated, coil springs, under repetitive use and strain (load), develop creep and fatigue due to the continual motion of the spring during compressing and elongating. That is, the physical structure of the coil spring is in continual motion. However, actuators 100 and 200 replace the coil spring with magnets oriented in a repulsive state. Since the repulsive force is an inherent nature of magnets, relying upon the repulsive force to return the respective systems to a rest state does not require any motion in the physical structure of the magnets. Consequently, no creep or fatigue develops in magnets under the use of inherent repulsive force. In fact, over time, there is no change in the magnetic power of the repulsive force used to return the respective systems to their respective rest states. Therefore, the desired characteristic quality of a musical sound will continually and consistently be produced.

Moreover, the force versus displacement gradient of a compressed coil spring is substantially linear while the force versus displacement gradient for spacing magnets in a repulsive state is non-linear. Accordingly, adjusting the spacing between magnets in systems with actuators 100 and 200 can decrease the response time for the actuators to move the upper cymbal away from the lower cymbal.

It should be understood that either embodiment of cymbal systems with actuators 100 and 200 are configured to be easily secured to any conventional cymbal stand, for example, a hi hat cymbal system. That is, actuators 100 and 200 can be used as a universal replacement structures for the upper tube assembly of any cymbal stand, existing now or in the future. Moreover, the actuators 100 and 200 can replace the tension control mechanisms currently used today or in the future.

Still further, while embodiments of cymbal systems described with respect to actuators 100 and 200 places the collection of magnets integral to the upper column of a cymbal stand. However, alternate methods could place the collection of magnets in the lower column, or even external and spaced from the cymbal stands.

Exemplary magnets that can be used in actuators 100 and 200 include rare-earth magnets. Rare-earth magnets are strong permanent magnets made from alloys of rare earth elements in the lanthanide series (plus scandium and yttrium). Other magnets can be used for actuators 100 and 200 such as ferrite or alnico magnets, but these magnets do not produce magnetic fields as strong (which correlates to the strength of the repulsive and attractive forces) as rare-earth magnets. There are two types of rare-earth magnets and both can be used for actuators 100 and 200: neodymium magnets and samarium-cobalt magnets.

Still other configurations for magnets that can be used in actuators 100 and 200 include electromagnets.

It should be understood that the magnetic assemblies described with respect to actuator 100 can be used in place of at least one of the magnets described for actuator 200, and vice versa. Accordingly, actuator 100 can have one or more magnetic assemblies 160 and one or more of magnets 206. Similarly, actuator 200 can have one or more magnetic assemblies 160 and one or more of magnets 206.

Still further, each actuator 100 and 200 requires at least two magnets 206, or at least two magnetic assemblies 160, or a combination of one magnet 206 and one magnetic assembly 160 to produce the desired repulsive force. However, each actuator 100 and 200 can have a collection of 3, 4, 5, 6, 7, 8, 9, or more of the magnets 206 and magnetic assemblies 160, and in any combination.

In compliance with the statute, the various embodiments have been described in language more or less specific as to structural and methodical features. It is to be understood, however, that the various embodiments are not limited to the specific features shown and described, since the means herein disclosed comprise disclosures of putting the various embodiments into effect. The various embodiments are, therefore, claimed in any of its forms or modifications within the proper scope of the appended claims appropriately interpreted in accordance with the doctrine of equivalents.

What is claimed is:

1. A musical instrument actuator comprising:
   a first magnet;
   a second magnet spaced from the first magnet in a repulsive relationship;
   a third magnet spaced from the second magnet in a repulsive relationship; and
   a rod configured for axial movement through each magnet and secured to a musical instrument, the rod in a corresponding movement relationship with the first, second and third magnets, the corresponding movement relationship comprising movement of the rod corresponds to movement between the first, second and third magnets.

2. The actuator of claim 1 wherein the musical instrument is a cymbal.

3. The actuator of claim 1 wherein the musical instrument is a cymbal and further comprising a second cymbal in sliding engagement with the rod.

4. The actuator of claim 1 wherein at least one of the first and second magnets comprises at least one of the following type of magnets: neodymium magnets and samarium-cobalt magnets.

5. The actuator of claim 1 further comprising a fourth magnet coaxially aligned over the rod and in a repulsive relationship with the third magnet.

6. The actuator of claim 1 wherein the rod is a pull rod in a cymbal stand.

7. The actuator of claim 1 wherein the musical instrument is a hi hat cymbal stand and wherein the rod is a pull rod in the cymbal stand.

8. The actuator of claim 1 further comprising a tubular housing surrounding the magnets and at least a portion of the rod.

9. The actuator of claim 1 further comprising a locking screw in a locking relationship with the rod.

10. The actuator of claim 1 further comprising a tilt mechanism in a tilting relationship with the rod.

11. A method for actuating a musical instrument comprising:
   providing a cymbal stand comprising:
      a pull rod coupled to a foot pedal and coupled to a first cymbal of a pair of cymbals, a second cymbal of the pair of cymbals proximate the first cymbal wherein the first cymbal moves toward the second cymbal upon pressing the foot pedal; and at least three magnets coaxially aligned over the pull rod in a corresponding movement relationship with the pull rod, the corresponding movement relationship comprising movement of the pull rod corresponding to movement between the magnets, each magnet being spaced from each other in a repulsive state; and pressing the foot pedal to move the pull rod and drive the first cymbal toward the second cymbal.

12. The method of claim 11 further comprising releasing the pressing of the foot pedal wherein the repulsive force between the magnets moves the pull rod axially in an opposite direction to drive the cymbals apart.

13. The method of claim 11 further comprising adjusting the spacing between the magnets to adjust the force needed to move the foot pedal.

14. The actuator of claim 11 wherein at least one of the magnets comprises at least one of the following type of magnets: neodymium magnets and samarium-cobalt magnets.

15. The actuator of claim 11 further comprising providing a tubular housing to at least surround the magnets.

16. The actuator of claim 11 further comprising providing a locking screw in a locking relationship with the rod.

17. The actuator of claim 11 further comprising providing a tilt mechanism in a tilting relationship with the rod.

18. A musical instrument actuator comprising:
 a first magnet assembly comprising a first magnet in an attractive relationship with a second magnet;
 a third magnet in a repulsive relationship with the first magnet assembly; and
 a rod extending through each magnet of the first magnet assembly and the third magnet, the rod configured for axial movement that corresponds to axial movement of the first magnet assembly and the third magnet.

19. The actuator of claim 18 further comprising a fourth magnet, the fourth and third magnets comprising a second magnet assembly, the second magnet assembly in a repulsive relationship with the first magnet assembly.

20. The actuator of claim 18 further comprising a locking screw in a locking relationship with the rod.

* * * * *

UNITED STATES PATENT AND TRADEMARK OFFICE
CERTIFICATE OF CORRECTION

PATENT NO. : 9,870,761 B2
APPLICATION NO. : 15/250862
DATED : January 16, 2018
INVENTOR(S) : Robert R. Spencer It is certified that error appears in the above-identified patent and that said Letters Patent is hereby corrected as shown below:

Column 3, Line 21 - Replace "foot way from" with --foot away from--

Column 7, Lines 62-63 - Replace "foot petal 26" with --foot pedal 26--

Column 9, Line 25 - Replace "use the of inherent" with --use of the inherent--

Signed and Sealed this
Seventeenth Day of April, 2018

Andrei Iancu
*Director of the United States Patent and Trademark Office*